(12) United States Patent
Kuehn et al.

(10) Patent No.: US 6,743,239 B1
(45) Date of Patent: Jun. 1, 2004

(54) DEVICES WITH A BENDABLE TIP FOR MEDICAL PROCEDURES

(75) Inventors: Stephen T. Kuehn, Woodbury, MN (US); Karen P. Montpetit, St. Paul, MN (US)

(73) Assignee: St. Jude Medical, Inc., St. Paul, MN (US)

(*) Notice: Subject to any disclaimer, the term of this patent is extended or adjusted under 35 U.S.C. 154(b) by 0 days.

(21) Appl. No.: 09/578,984

(22) Filed: May 25, 2000

(51) Int. Cl.$^7$ .............................. A61B 17/04; A61B 1/00

(52) U.S. Cl. ..................... 606/139; 606/101; 606/208; 600/101; 600/139; 600/141

(58) Field of Search .................. 606/1, 51, 52, 606/108, 170, 171, 174, 180, 169, 205–210; 604/22; 600/101, 139, 146, 147, 562–567

(56) References Cited

U.S. PATENT DOCUMENTS

| | | | |
|---|---|---|---|
| 3,060,972 A | 10/1962 | Sheldon | 138/120 |
| 3,557,780 A | 1/1971 | Sato | 128/4 |
| 3,585,885 A | * 6/1971 | Carr | |
| 3,625,200 A | 12/1971 | Muller | 128/2.05 R |
| 3,674,014 A | 7/1972 | Tillander | 128/2.05 R |
| 4,686,963 A | 8/1987 | Cohen et al. | 128/4 |
| 4,773,395 A | 9/1988 | Suzuki et al. | 128/4 |
| 4,815,476 A | * 3/1989 | Clossick | 606/174 |
| 5,042,707 A | 8/1991 | Taheri | |
| 5,174,276 A | 12/1992 | Crockard | |
| 5,209,756 A | 5/1993 | Seedhom et al. | 606/151 |
| 5,282,810 A | 2/1994 | Allen et al. | 606/150 |
| 5,411,508 A | * 5/1995 | Bessler et al. | 227/179.1 |
| 5,417,700 A | 5/1995 | Egan | 606/144 |
| 5,423,858 A | 6/1995 | Bolanos et al. | 606/220 |
| 5,441,483 A | 8/1995 | Avitall | 604/95 |
| 5,441,499 A | 8/1995 | Fritzsch | 606/45 |
| 5,448,989 A | 9/1995 | Heckele | 600/142 |
| 5,454,827 A | * 10/1995 | Aust et al. | 606/170 |

(List continued on next page.)

FOREIGN PATENT DOCUMENTS

| | | |
|---|---|---|
| DE | 42 22 121 C 1 | 9/1993 |
| DE | 42 43 715 A 1 | 7/1994 |
| EP | 0 684 012 A2 | 2/1995 |
| WO | WO 93/00048 | * 1/1993 |
| WO | WO 94/18881 | 9/1994 |
| WO | WO 97/39688 | 10/1997 |
| WO | WO 98/07375 | 2/1998 |
| WO | WO 98/30153 | 7/1998 |
| WO | WO 99/13777 | 3/1999 |

OTHER PUBLICATIONS

Written Opinion dated Jul. 9, 2002 (PCT/US01/15905).
Invitation to Pay Additional Fees (PCT/US01/19505), dated Nov. 15, 2001.
"Mitral Valve Reconstruction for Mitral Insufficiency" by Ross M. Reul et al., for *Progress in Cardioascular Diseases*, vol. XXXIX, No. 6, (May/Jun.) 1997, pp. 567–599.
Daig Brochure: "Schwartz™ Introducers", Daig Corporation, Minnetonka, MN 1995.
Daig Brochure: "Daig Fast–Cath™ Introducers", Daig Corporation, Minnetonka, MN 1994.
"The edge–to–edge technique: A Simplified Method to Correct Mitral Insufficiency", by F. Maisano et al, for *European Journal of Cardio–thoracic Surgery*, 13:240–246, 1998.

*Primary Examiner*—Gary Jackson
(74) *Attorney, Agent, or Firm*—Altera Group, LLC; Hallie A. Finucane

(57) ABSTRACT

An improved device for performing medical procedures, preferably minimally invasive medical procedures, includes a shaft with a proximal and distal end and a bendable tip extending from the distal end of the shaft. In some preferred embodiments, a fastener applicator extends from the bendable tip. In other preferred embodiments, a malleable section is located between the bendable tip and the shaft. The bendable tip can include a plurality of articulating segments. The improved directional device can be used to repair native valves in a patient, especially heart valves.

49 Claims, 10 Drawing Sheets

U.S. PATENT DOCUMENTS

| | | | |
|---|---|---|---|
| 5,478,353 A | 12/1995 | Yoon | 606/213 |
| 5,522,788 A * | 6/1996 | Kuzmak | 606/141 |
| 5,549,637 A * | 8/1996 | Crainich | 606/207 |
| 5,666,970 A | 9/1997 | Smith | 128/772 |
| 5,713,910 A | 2/1998 | Gordon et al. | 606/139 |
| 5,749,828 A | 5/1998 | Solomon et al. | 600/141 |
| 5,797,927 A | 8/1998 | Yoon | 606/144 |
| 5,810,716 A | 9/1998 | Mukherjee et al. | 600/146 |
| 5,810,847 A | 9/1998 | Laufer et al. | 606/142 |
| 5,836,960 A * | 11/1998 | Kolesa et al. | 606/174 |
| 5,897,487 A | 4/1999 | Ouchi | |
| 5,919,199 A | 7/1999 | Mers Kelly et al. | 606/139 |
| 5,947,363 A | 9/1999 | Bolduc et al. | 227/176.1 |
| 5,989,182 A | 11/1999 | Hori et al. | |
| 6,139,563 A * | 10/2000 | Cosgrove, III et al. | 606/205 |
| 6,152,894 A * | 11/2000 | Kubler | 604/22 |

* cited by examiner

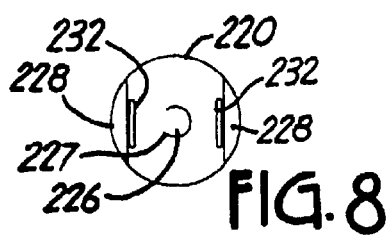
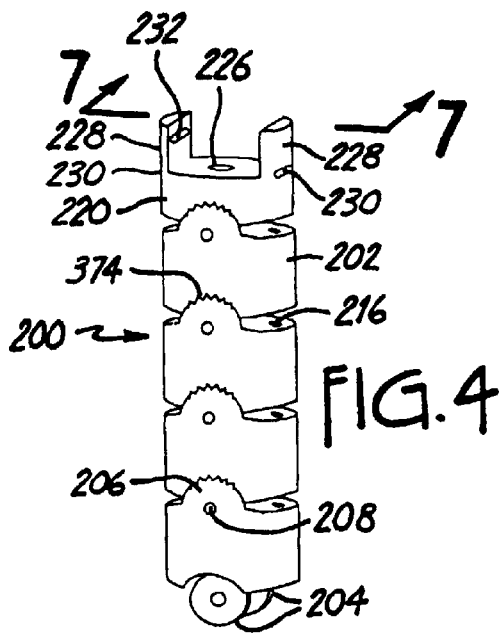
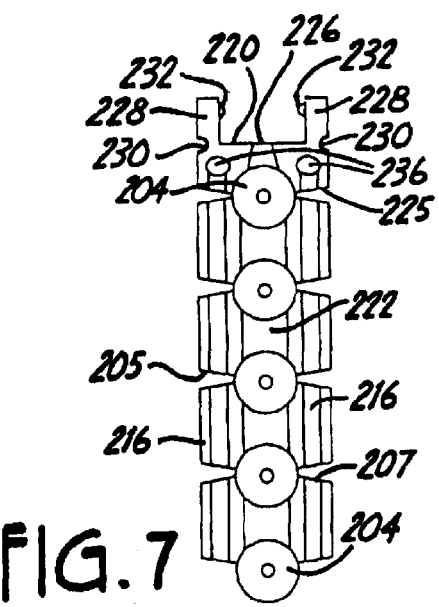
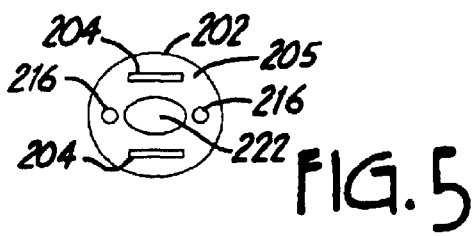
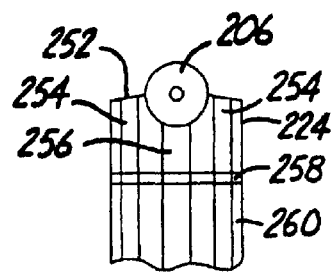
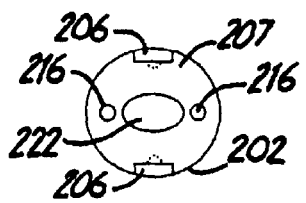

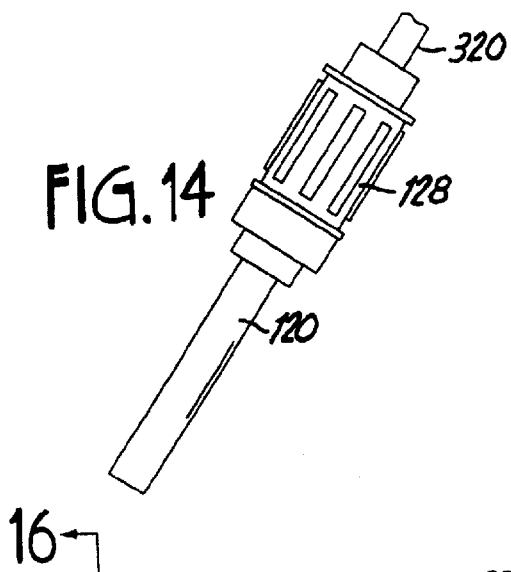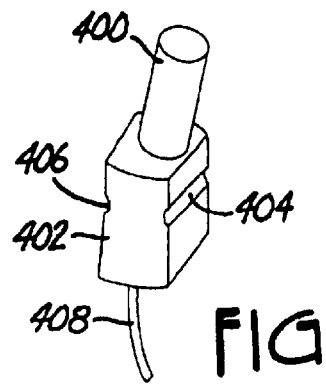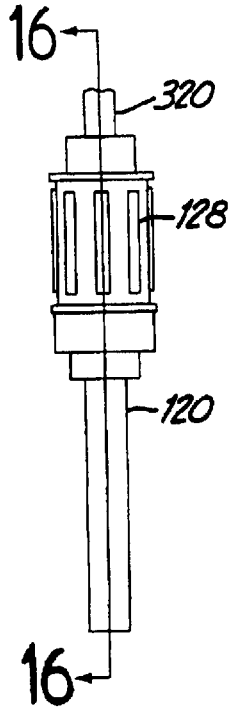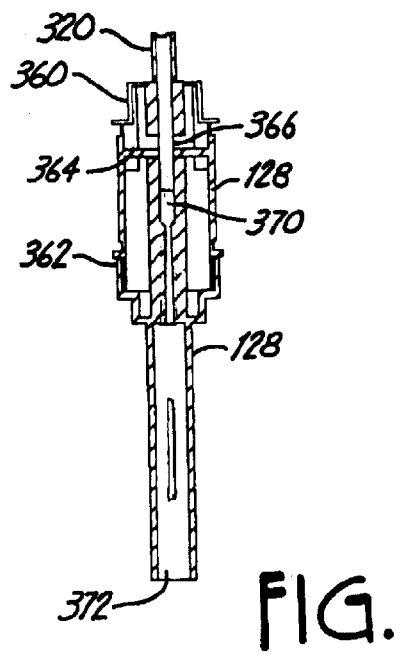
FIG. 14
FIG. 17
FIG. 15
FIG. 16A

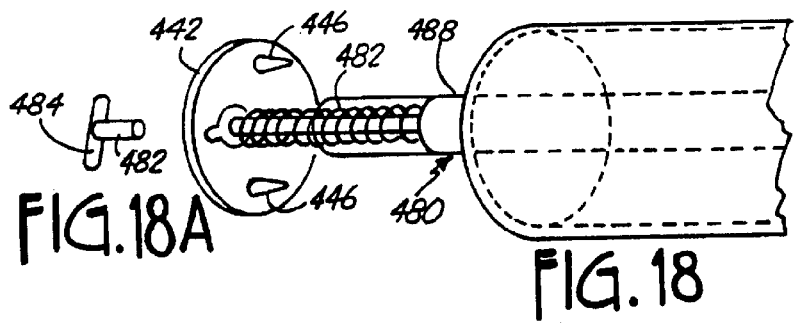
FIG. 18A  FIG. 18
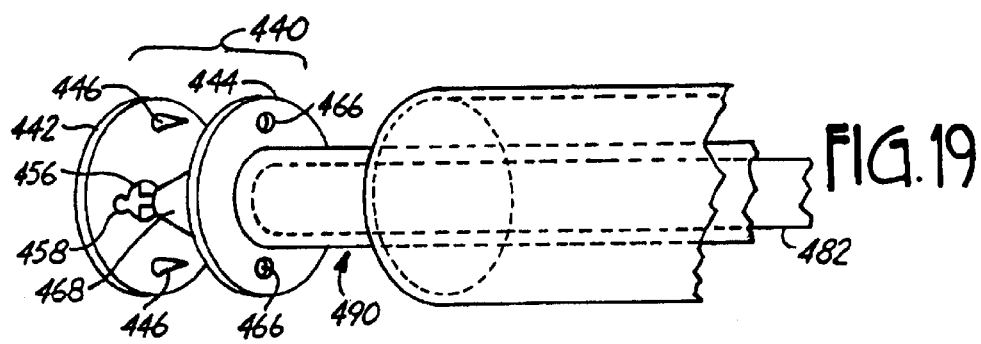
FIG. 19
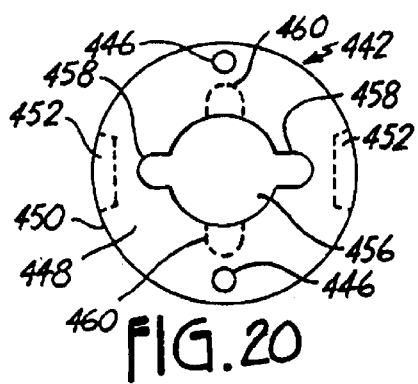
FIG. 20  FIG. 21  FIG. 25
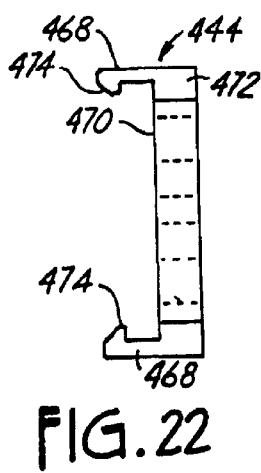
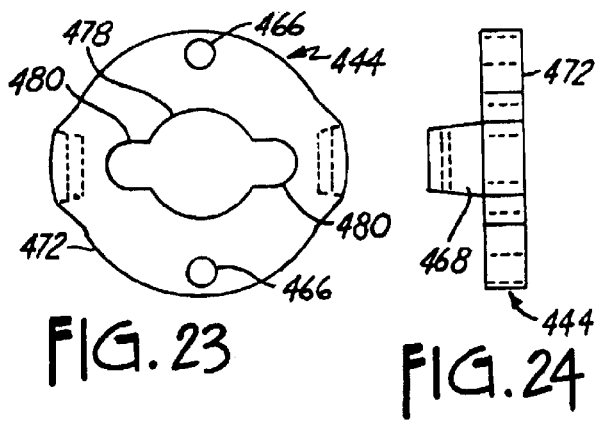
FIG. 22  FIG. 23  FIG. 24

DEVICES WITH A BENDABLE TIP FOR MEDICAL PROCEDURES

BACKGROUND OF THE INVENTION

The invention relates to medical devices or tools for performing surgical procedures, including heart valve repairs. In particular, the invention relates to devices with bendable tips for positioning medical instruments during invasive procedures, preferably minimally invasive procedures.

Endoscopes, orthoscopes, probes, catheters and the like can be inserted into a patient for the performance of various medical procedures. To perform the procedure, a particular instrument is positioned at the appropriate location within the patient. The procedure can involve one or more processes, such as imaging, tissue ablation, tissue repair, tissue cutting and combinations thereof. These procedures can involve vascular, intestinal, urological, vaginal, oral or percutaneous delivery of the instrument to the specific location for performing the procedure. Procedures for the repair of a damaged or diseased heart, especially to correct heart valve insufficiency, are of particular interest.

Heart valve insufficiency can be a debilitating and possibly life threatening condition. For example, heart valve regurgitation, i.e., backward leakage of blood at a heart valve, results in reduced pumping efficiency. With respect to mitral valve regurgitation, compensatory mechanisms such as hypertrophy and dilation of the ventricle suggest early treatment to prevent progressive deterioration of ventricular function. Diagnosis of mitral regurgitation can be performed using visualization with transesophageal echocardiography or by echocardiography. In particular, defective leaflet coaptation and the site and direction of the regurgitant flow can be examined to evaluate likely modes of failure.

Mitral valve prolapse, i.e., myxomatous degeneration of mitral valve leaflets, is the most common cause of mitral regurgitation in North America. Rheumatic heart disease was the most common cause of mitral regurgitation in the U.S.A. thirty years ago and is still the most common cause of mitral regurgitation in developing countries. Chronic rheumatic heart disease results in retraction, deformity and rigidity of one or both mitral valve cusps as well as structural abnormalities in the commissures, chordae tendineae and papillary muscles. Ischemic mitral regurgitation (IMR), i.e., anemia of the valve tissue due to reduced arterial blood flow feeding the valve tissue, is the second most common cause of mitral regurgitation. Studies suggest that annular irregularities and posterior papillary muscle fibrosis with scarring of the underlying ventricular wall may be associated with IMR.

Many cases of mitral regurgitation can be repaired by modifications of the original valve in a procedure generally referred to as valvuloplasty. These repair procedures typically involve a full sternotomy and quadrangular resection of the anterior leaflet, while on cardiopulmonary bypass. Repairs can also involve reattachment of chordae tendineae, which tether the valve leaflets, or removal of leaflet tissue to correct misshapen or enlarged valve leaflets. In some cases, the annulus of the valve is secured using an annuloplasty ring. Valves that are heavily calcified or significantly compromised by disease may need to be replaced.

As an alternative to these repair techniques, an edge-to-edge suturing of the anterior and posterior mitral valve leaflets can be performed. Commonly referred to as a "bow-tie" repair, edge-to-edge suturing ensures leaflet, coaptation without performing a quadrangular resection of the anterior leaflet. The bow-tie repair generally involves the use of a centrally located suture, although a suture can be placed close to a commissure, or multiple sutures can be used to complete the repair. A centrally placed suture creates a double orifice valve, which resembles a bow-tie.

The edge-to-edge repair procedure has been applied using invasive procedures by placing the patient on extracorporeal circulation. An incision is made to provide access into the left atrium of the heart. Following suturing, the atrium is closed. Such repairs can result in a significant decrease in mitral regurgitation along with a corresponding increase in the ejection fraction. Corresponding repairs can be performed on tricuspid valves.

SUMMARY OF THE INVENTION

In a first aspect, the invention pertains to a device for medical procedures comprising a shaft, a bendable tip and a fastener applicator. The shaft has a distal end and a proximal end. The bendable tip extends from the distal end of the shaft. The fastener applicator extends from the bendable tip. In some embodiments, the bendable tip includes a plurality of articulating segments.

In a further aspect, the invention pertains to a device for medical procedures comprising a shaft, a malleable section, a bendable tip and a control mechanism. The shaft has a distal end and a proximal end. The malleable section extends from the distal end of the shaft. The bendable tip extends from the malleable section. The control mechanism is connected to the bendable tip wherein the control mechanism comprises a knob. The adjustment of the knob controls the bend of the bendable tip.

In another aspect, the invention pertains to a device for medical procedures comprising a shaft, a bendable tip, a handle, a knob and a cord. The shaft has a distal end and a proximal end. The tip extends from the distal end of the shaft. The handle has a grip generally coaxial with the shaft, and the handle is attached to the proximal end of the shaft. The knob rotates around the axis of the grip. The cord connects the tip with the knob such that rotation of the knob in one direction retracts the cord to bend the tip.

In addition, the invention pertains to a method of repairing a heart valve including inserting a device through the catheter and performing a repair of the heart valve with the medical instrument. The device includes a shaft, a bendable tip extending from the distal end of the shaft and a medical instrument extending from the bendable tip. In some embodiments, the method includes placing a catheter extending within the heart, and the insertion of the device includes introducing the device through the catheter.

BRIEF DESCRIPTION OF THE DRAWINGS

FIG. 4 is a perspective view of a portion of an articulating tip.

FIG. 5 is a bottom view of a repeating segment in the articulating tip of FIG. 4.

FIG. 6 is a top view of a repeating segment of the articulating tip of FIG. 4.

FIG. 7 is a sectional view of the articulating tip of FIG. 4 taken along line 7—7 of FIG. 4.

FIG. 8 is a top view of the end element of the articulating tip of FIG. 4.

FIG. 9 is a fragmentary, sectional view of the bottom segment of the articulating tip and a portion of a shaft or malleable section connected to the bottom segment.

FIG. 14 is a perspective view of a handle and knob for use with a directional medical device with two control cords.

FIG. 15 is a side view of the handle and knob of FIG. 14.

FIG. 16A is a sectional view of the handle and knob of FIG. 14 taken along line 16—16 of FIG. 15.

FIG. 17 is a perspective view of a medical instrument that can be reversibly attached to the end segment of the articulating tip of FIG. 4.

FIG. 18 is a perspective view of a portion of a clip held by a deployment device at the tip of an directional medical device, the clip being useful for fastening heart valve leaflets.

FIG. 18A is a perspective view of the end of a first applicator used for deploying the clip.

FIG. 19 is a perspective view of the clip of FIG. 18 and associated deployment devices, with the two portions of the clip aligned.

FIG. 20 is a front view of a first portion of the clip of FIG. 19.

FIG. 21 is a side view of the first portion of the clip of FIG. 19.

FIG. 22 is a side view of the second portion of the clip of FIG. 19.

FIG. 23 is a rear view of the second portion of the clip of FIG. 19.

FIG. 24 is a side view of the second portion of the clip of FIG. 19 rotated 90 degrees relative to the view in FIG. 22.

FIG. 25 is a side view of the two portions of the clip of FIG. 19 fastened together.

DETAILED DESCRIPTION OF THE ILLUSTRATIVE EMBODIMENTS

Figure 1:
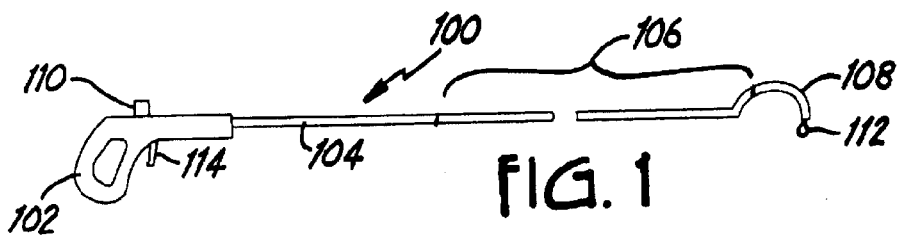
FIG. 1 is a side view of a directional medical device with a bendable tip.

An improved steerable tip for a surgical device useful in medical procedures, including less invasive procedures, provides easy to control bending of the tip. The steerable tip can be located on a shaft for the performance of less invasive medical procedures, commonly referred to as minimally invasive procedures. However, the device can also be used in open cavity procedures. The steerable tip preferably includes pivoting, articulating segments that can be locked at a selected degree of bending. The directional device can further include a malleable section that provides a coarse position adjustment of the bent tip.

An instrument for the performance of a surgical procedure is generally positioned at the bendable tip. In preferred embodiments, a fastener applicator extends from a steerable, articulating tip. The fastener applicator can be used, for example, to perform heart valve repair, such as edge-to-edge heart valve leaflet fastening.

The preferred medical devices with a bendable tip, i.e. directional medical devices, include a relatively thin extension that can be projected into a patient. The patient is generally a mammal such as, a horse, a cow, a pig, a sheep, a dog, a cat, and preferably is a human. The steerable tip is located at the distal end of the shaft and a handle is located at the proximal end. The steering of the tip generally is controlled with a knob at or near the handle. Thus, the directional devices can be used for the performance of less invasive procedures in which the device is introduced into the patient such that the tip is located within the patient. The extension, which includes the shaft and optional malleable section, may be located partially within and partially external to the patient. Manipulations at the proximal end control the steering of the tip and manipulation of the instrument(s) used in the procedure.

The directional medical device generally includes a handle, a knob, a shaft, an optional malleable section and an articulating tip. The handle can be used by the surgeon to move the device into position. The knob is connected appropriately to the tip through a control mechanism such that movement of the knob at the proximal end alters the bending of the tip at the distal end of the device. The knob generally is attached at or near the handle such that the surgeon can easily move the knob to change the orientation of the tip. The shaft has appropriate dimensions for the corresponding procedure to be performed. The shaft is generally flexible such that gentle curves in the body can be negotiated during introduction of the device into the body.

The directional device can optionally include a malleable section between the shaft and the articulating tip. The malleable section, for example, can be made from a deformable polymer, memory metal or a soft metal. If a malleable section is used, the shaft can be short. The malleable section is bent manually prior to use of the device in the procedure. Bending of the malleable section provides for a gross direction of the tip. A malleable section is most useful for procedures performed in open cavities.

The articulating tip preferably includes a plurality of articulating segments or vertebrae that pivot relative to each other. Preferred articulating tips can bend in a plane in either direction relative to a straight orientation. In preferred embodiments, the tip can be locked into a particular bent position. The articulating tip is connected by way of cords or other transmission devices to the knob at the proximal end of the device such that the knob can be used to control the bending of the tip at the distal end.

A suitable instrument(s) can be mounted at or near the tip for performing the medical procedure. The instruments can be permanently mounted at the tip of the medical device with control of the instrument being provided at the proximal end of the directional device. Alternatively, the instrument can be reversibly mounted at the tip prior to beginning a procedure. In alternative embodiments, the directional medical device has an open lumen to provide for the introduction of instruments from the proximal end through the lumen to the tip. In this way, instruments can be introduced and/or changed during the procedure, and a wider range of instruments can be used since some instruments may require manipulation by moving one or more components of the instrument into position through the open lumen.

The directional medical device can be used for the delivery of a variety of instruments into a patient for the performance of less invasive, such as minimally invasive, medical procedures. Suitable instruments include, for example, lenses or transducers for imaging, visualization or laser transmission, electrodes for tissue ablation, electrodes for cauterization, ultrasound probes, grippers, fasteners, cutting blades, forceps and combinations thereof. For the performance of certain procedures, it may be useful or necessary to steer the instrument to a particular location within the patient. Depending on the delivery approach, this may require bending of a tip at the end of a shaft. However, for certain procedures, the tip must lock into position such that performance of the procedure can be successfully performed. In particular, forces applied against the tip by the instrument can move the tip if it is not locked into place.

A plurality of instruments can be positioned at or near the bending tip. For example, a visualization device, such as a lens at the end of a fiber optic element, along with an ablation element can be located at the tip. A variety of combinations of instruments can be combined to achieve desired results.

Generally, the directional medical device is introduced into the patient using a catheter, introducer and the like. The appropriate characteristics of the catheter and the directional medical device depend on the point of introduction and the point of deployment. In particular, the length and thickness of the directional medical device must be consistent with the path for placing the device within the body.

The improved directional medical devices can be useful for a variety of percutaneous procedures, such as laparoscopies as well as other forms of less invasive surgical techniques, cardiovascular and vascular manipulations, ligament manipulations, intestinal manipulations and manipulations performed by way of oral, urological, esophagal or vaginal introduction. Entrance to the particular location to perform the surgical procedure can be performed using conventional approaches. Preferred procedures include, for example, heart repair, especially heart valve repair. Heart valve repairs can be performed by way of a vascular approach or through the chest.

Methods have been developed for performing less invasive heart valve repairs, including repairs to the mitral and tricuspid valves. In particular, the repairs can be performed on a beating heart such that the patient does not have to be placed on cardiopulmonary bypass. While the discussion below focuses on the repair of mitral heart valves, the repair approaches can be used for the repair of tricuspid valves using straightforward modification of the described procedures and instruments to take into account anatomical constraints. These procedures are discussed further in copending and commonly assigned U.S. patent application Ser. No. 09/115,820, now U.S. Pat. No. 6,165,183, entitled "Mitral and Tricuspid Valve Repair," incorporated herein by reference.

Access into the heart for mitral valve repair is obtained by securing a passageway from the exterior of the body into the body and into the heart to provide access into the left atrium or left ventricle. With suitable instruments inserted through the passageway, the mitral leaflets are grabbed, and the edges of the leaflets are secured together. The gripping and securing or fastening procedures can be performed simultaneously in some embodiments of the invention, or they can be performed separately. A suitable method of visualization may be used to guide the manipulations. Manipulations to the mitral valve can be conducted under ultrasound or fluoroscopy to show correct placement of the devices and of the repair and to verify effectiveness of the repair.

One approach to introduce the surgical instruments into the heart involves the direct introduction of a passageway through the wall of the heart. To introduce the passageway into the body, an incision is made in the chest or rib cage, and a cardiac catheter is placed into the incision. Tools generally used to position catheters can be used to guide the cardiac catheter to the heart and into the heart wall, as described further below. Use of properly selected tools for the introduction of the cardiac catheter reduces the amount of trauma to the heart. The directional medical devices with the bendable tips described herein can be inserted through the cardiac catheter to perform the repairs. Upon completion of the heart valve repair, the instruments are removed through the cardiac catheter, the cardiac catheter is removed, and the incision in the heart wall is repaired, for example, with suture.

Alternatively, the surgical instruments can be introduced into the heart by a vascular approach. In these approaches, a vascular catheter is introduced into an artery or vein and directed into the heart. These vascular approaches are described further below.

Suitable gripping and fastening instruments have appropriate dimensions to fit through the cardiac or vascular catheter into the heart. The instruments can be part of a directional medical device with a bendable tip, as described herein. Alternatively, the instruments can be introduced into the lumen of the device for positioning at or near the bendable tip.

If the instruments are introduced through the lumen of a medical device with a bendable tip, the instruments generally have a shaft between a distal end and a proximal end. The shaft may be flexible. The distal end of the instrument is inserted through the medical device such that the instrument protrudes at or near the bendable tip. The gripping and/or securing/fastening elements are located at the distal end of the instrument. One or more actuating elements are located at the proximal end.

In some embodiments for performing heart valve repair, a single element performs the gripping and fastening functions. In other words, a fastening element grips the tissue during the fastening process such that a separately identifiable gripping element is not present. For example, suture can be placed through each leaflet such that tightening of the suture draws the two portions of the leaflets together.

Alternatively, the gripping and fastening elements can be distinct, separate instruments. These can both be located at the end of a medical device with a bendable tip. Alternatively, they can be simultaneously introduced through the lumen of the directional medical device. For certain embodiments involving the introduction of instruments through the lumen of the directional medical device, functionally distinct gripping and fastening elements can be integrated into a single structure. Alternatively, the distinct gripping and fastening elements can be located on separate structures, such that the two elements can be inserted simultaneously through the lumen of the medical device. The directional medical device can have a single lumen or multiple lumens for the introduction of medical instruments. Alternatively, one or more additional medical devices with bendable tips can be introduced into the heart to provide separate instrument passageways for the gripping and fastening instruments and any other instruments used to facilitate the procedure and/or to provide visualization.

Medical Device with a Bendable Tip

The improved directional medical device has a bendable tip to provide appropriate orientation for the performance of a medical procedure. In preferred embodiments, the bendable tip has articulating segments that can be locked into position. Furthermore, preferred bendable tips can bend in either of two directions such that various positions within a plane can be reached by selecting the degree and direction of bending of the tip. Easy to manipulate control knobs preferably can be used to regulate the degree of bending of the tip. A malleable section can be included between the bendable tip and a shaft. The malleable section provides a gross manipulation for positioning the bendable tip for use of the device in certain locations within the patient, especially in open cavity procedures.

An improved directional medical device, as described herein, is depicted schematically in FIG. 1. Device 100 includes a handle 102, a shaft 104, an optional malleable section 106, a bendable tip 108, a knob 110, an optional medical instrument 112, and an optional actuator 114 for controlling instrument 112. Furthermore, directional device 100 includes a control mechanism that allows for control of the bending of tip 108 by movement of knob 110.

Generally, handle 102 includes an opening to a central lumen that extends to bendable tip 108. This opening to the central lumen preferably includes a hemostasis valve to prevent blood from flowing out of the device. Standard designs used in the catheter art can be used for the hemostasis valve.

Figure 2:
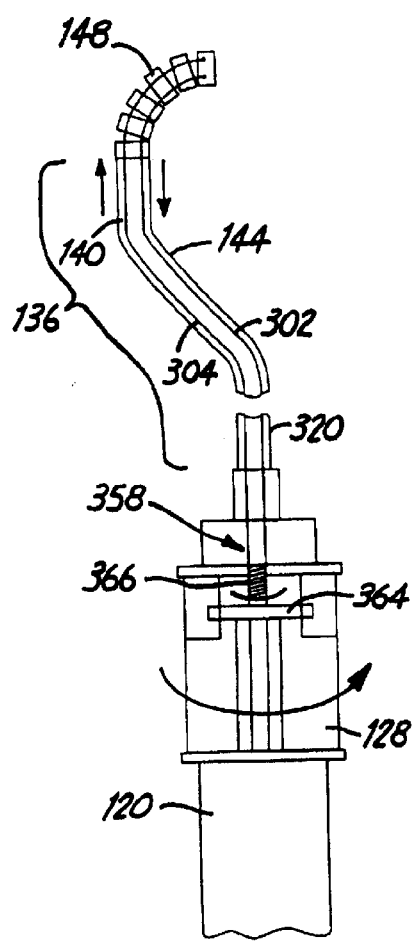
FIG. 2 is a side view of an embodiment of a directional medical device having a control mechanism with two cords, some hidden structure being shown for clarity.
Figure 3:
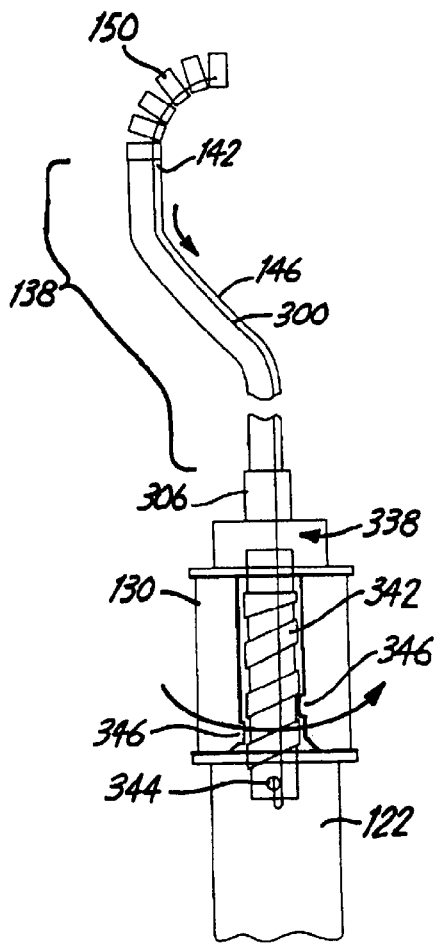
FIG. 3 is a side view of an alternative embodiment of a directional medical device having a control mechanism with one cord, some hidden structure being shown for clarity.

Handle 102 is located at the proximal end of directional device 100. Handle 102 can have any convenient configuration. Two preferred embodiments of handle 102 are shown in FIGS. 2 and 3, respectively. Handles 120 (FIG. 2) and 122 (FIG. 3) have a generally cylindrical gripping section. Two easy to control knobs 128, 130, connect handles 120, 122 with respective shafts. The interface of knobs 128, 130 with a control mechanism is described further below.

Referring to FIG. 1, shaft 104 generally has a length and thickness consistent with its intended use. If device 100 includes a malleable section 106, shaft 104 may be short since shaft 104 provides for connection between handle 102 and malleable section 106. If no malleable section 106 is present, shaft 104 provides for the placement of the tip at its desired location, so that shaft 104 then needs to have a sufficient length for this purpose. For example, if the device is intended for vascular entry into the heart, the shaft must be long enough to reach the heart from the intended entry point into the vascular system. If shaft has a significant length, shaft 104 generally is somewhat flexible such that tip 108 can be guided to the location for the performance of the procedure. For example, for a vascular entry, shaft 104 should be flexible enough to follow the vascular system to the vicinity of the procedure. Similarly, for other delivery approaches, shaft 104 may need to follow gentle curves in the body to reach its destination.

Shaft 104 can be constructed from similar materials and using similar techniques as used for the productions of corresponding components of catheters and the like. In particular, the wall of shaft 104 can have one or more layers. At least one of the layers generally is made from a rigid plastic or a suitable metal, such as stainless steel or titanium. The inside of shaft 104 can include appropriate support structures for the control mechanism and an open central lumen or lumens. Shaft 104 can be very short if a malleable section 106 is included. In other embodiments, shaft 104 must belong enough to carry the tip to its intended location.

Malleable section 106 is located between shaft 104 and tip 108. The presence of a malleable section is optional. The malleable section is designed for adjustment independent of tip 108 and provides for gross positioning of the device in the body which can involve an approach to a specific site for a procedure. The malleable section can include most of the distance between the distal and proximal ends of the device, or the malleable section can be a shorter section near the tip.

Suitable materials for malleable section 106 can bend significant amounts in response to forces applied distal to malleable section 106 where malleable section 106 retains its shape when the forces are no longer applied. Malleable section 106 bends in response to larger forces but remains resilient against lesser forces. Thus, the bending of section 106 is very non-linear with respect to the application of forces. Malleable section 106 can be made from metals, flexible polymers or combinations thereof. Suitable metals include, for example, soft metals, such as soft stainless steel or copper, and spring metals, such as Elgiloy®, a cobalt chromium nickel alloy, aid MP35N, a nickel-cobalt-chromium-molybdenum alloy, and Nitinol®, a nickel-titanium alloy. Suitable flexible polymers include elastomers, thermoplastics and other polymers that can sustain significant flexure, bending, twisting and/or deformation without structural failure. Particularly preferred flexible polymer materials include, for example, polyurethane. Polymers for malleable section 106 can be formed in an accordion configuration to impart added malleability to the section. Generally, the malleable section is bent manually and holds its position in that configuration. Therefore, appropriate materials hold a shape once bent into that shape. The manually induced bend may only occur in a small portion of the malleable section.

As shown in FIGS. 2 and 3, malleable sections 136, 138 can include a straight section 140, 142 as well as a bending portion 144, 146. A straight section 140 can be used as part of a malleable section to separate the bending of the tip from the bending of the malleable section. The presence of a straight section provides a connection point between the malleable section and the bent tip.

Bendable tips can have various structures that provide for the bending of the tip in response to forces from the control mechanism. For example, bendable tips can be formed from malleable metals or polymers that bend in response to off axis tension applied to the tip. Alternatively, the tip can include accordion pleated metals or polymers that bend in response to forces applied by the control mechanism. In preferred embodiments, bendable tips 148, 150 include articulating segments, as shown in FIGS. 2 and 3. A variety of constructions of the articulating segments can be used. A preferred embodiment of a bendable tip with articulating segments is shown in FIGS. 4–7. As shown in the perspective view of FIG. 4, articulating tip 200 includes repeating segments 202 with interlocking hinges. A bottom view of a repeating segment is shown in FIG. 5, and a top view is shown in FIG. 6.

Two inner hinge elements 204 project from bottom surface 205 of each repeating segment 202, and two outer hinge elements 206 project from top surface 207 of each repeating segment 202. The location of the top and bottom hinge elements of the repeating segments 202 can be reversed without altering the function of the pivot as long as the connections of the pivots at the ends are correspondingly adjusted. Each inner hinge element 204 and outer hinge element 206 can include a hole through which a pin 208 is inserted to hold the hinge together. A hinge pivots around pin 208. Alternatively, the hinge elements can snap together without separate pins to pivot similarly around the snaps. Prong components of the snaps are shown in phantom lines in FIG. 6, and the prongs can snap into holes in inner hinge elements 204. The hinges allow tip 200 to pivot in either of two opposite directions along a plane such that the end of the tip can be oriented as desired in a plane.

Repeating segments 2202 further include channels 216. Channels 216 extend through the entire segment 202, as shown in the sectional view of FIG. 7. Repeating segments 202 can include a single channel, two channels, as shown in the FIGS. 5–6, or more than two channels. The use of two channels permits locking of the tip at a desired degree of bending and a greater degree of bending, i.e., a larger range of motion that can extend up to 180°. Channels 216 are off center and generally are located near an edge of repeating segment 202. Channels are used for elements of a control mechanism extending between the knob and end segment 220. The control mechanism, discussed further below, controls the degree of bending of tip 200. Also, each repeating segment 202 includes an open central lumen 222. Lumen 222 preferably has an oval or similar elongated shape with its major axis oriented toward channels 216. With an elongated shape, the lumen can better accommodate a cylindrical instrument when the tip is bent.

In FIGS. 4 and 7, four repeating segments are shown. Articulating tip 200 can include more or fewer repeating segments, as appropriate for the particular application. In preferred embodiments, adjacent segments pivot up to about 10° to 15° relative to each other. For most applications, a desired degree of bending is accessible with between about 4 and about 18 repeating segments, and generally between about 6 and about 9 repeating segments are appropriate. Articulating tip 200 includes an end segment 220, as the last segment, and a connecting segment 224 (FIG. 9), as a first segment that connects the tip to the rest of the device.

End segment 220 includes an open central lumen 226 that lines up with the central lumen 222 of repeating segments 202, as shown in FIG. 7. Preferably, central lumen 226 has an oval shape at bottom surface 225 that aligns with the oval central lumen 222 of repeating segments 202 and an asymmetrical opening 227 at the top, such as a D-shape as shown in FIG. 8. Asymmetrical opening 227 can align an instrument at a desired orientation at the tip. A top view of end segment 220 is shown in FIG. 8.

In some embodiments, end segment 220 also includes tabs 228, as shown in FIGS. 4, 7 and 8. Notches 230 provide some added resiliency to tabs 228. Prongs 232 extend inward from tabs 228. Tabs 228 can be used to secure instruments on the top of end segment 220 with prongs 232 helping to secure a medical instrument at the end of tip 200.

Inner hinge elements 204 project from bottom surface 225 of end segment 220. Inner hinge elements 204 connect with outer hinge elements 206 of the last repeating segment 202. Referring to FIG. 7, end segment 220 includes connectors 236 aligned with channels 216 for attachment to a control mechanism. Connectors 236 can simply be a cavity for holding a ball connector at the end of a cord. Alternative embodiments are described below.

Attachment segment 224 connects articulating tip 200 with the remaining portions of the device. Attachment segment 224 can be connected to malleable section 106, with or without a straight segment 140, 142, as shown in FIGS. 2 and 3, or directly to shaft 104 if there is no malleable section. In any case, attachment segment 224 can be a distinct element, or it can be formed as part of the adjacent element (malleable section or the shaft) connected to articulating tip 200.

A fragmentary, sectional side view of attachment segment 224 is shown in FIG. 9. A top view looks essentially as shown in FIG. 6 for a repeating segment 202. Outer hinge elements 206 project from top surface 252. Outer hinge elements 206 engage inner hinge elements 204 of the first repeat segment 202. Attachment segment 224 includes channels 254 that line up with channels 216 of repeating segments 202 and an open central lumen 256 that lines up with central lumen 222 of repeating segments 202. If attachment segment 224 is a distinct element, a weld, clamp, brace or other attachment device 258 connects attachment segment 224 with adjacent element 260 (malleable section or shaft), as shown in FIG. 9. The components of the articulating tip preferably are formed from rigid polymers, stainless steel, titanium or other biocompatible metals.

Referring to FIG. 1, knob 110 can have any of a variety of configurations. For example, knob 110 can include a lever or slide that pivots or slides to actuate bending of the tip. A control mechanism links knob 110 with bending tip 108, such that movement of knob 110 adjusts the degree of bending of tip 108. In some preferred embodiments, knob 110 is configured as a rotating cylindrical section 128, 130, as shown in FIGS. 2 and 3. In these embodiments, knobs 128, 130 rotate along an axis generally aligned with the axis of a cylindrical portion of handles 120, 122. Rotation of knobs 128, 130 result in adjustment of components of the control mechanism.

The control mechanism transfers an adjustment of the knob at the proximal end of the device to the tip where the degree of bending is altered according to the adjustment. Thus, the control mechanisms includes a communication conduit, such as one or more strands, cords, tubes or the like, to communicate movement of the knob to the tip. The control mechanism further includes a transfer device that converts movement of the knob to forces on the strands or other communication conduit. In some preferred embodiments, the control mechanism includes one or two cords that connect tip 108 with a distance varying component of the control mechanism. The cords can be formed from, for instance, stainless steel, titanium or other rigid metal, or from braided wire. An embodiment with one cord 300 is shown in FIG. 3, and an embodiment with two cords 302, 304 is shown in FIG. 2. Other embodiments may include more than two cords.

One end of the cord(s) is attached to the end segment of an articulating tip or comparable structure at the end of the tip for nonarticulating bendable tips. For example, in the structure shown in FIG. 7, balls at the end of cords fit into cavities 236 to secure the cords. Alternatively, the cords can be molded on or glued to the end segment. The other end of the cord is attached to the distance varying component of the control mechanism which applies appropriate tension to the cords to control the bending of the tip under the control of the knob.

Figure 10:
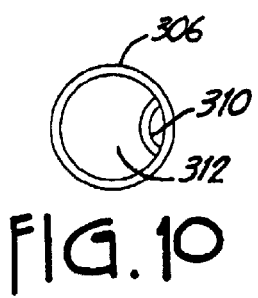
FIG. 10 is a sectional view of a shaft allowing for the passage of a single control cord, the cross section being taken perpendicular to the axis of the shaft.

Referring to FIG. 3, cord 300 extends from knob 130 through shaft 306 and malleable section 138. Shaft 306 can include guide loops 310 to guide the passage of cord 300, as shown in the cross section of shaft 306 in FIG. 10. Alternatively, shaft 306 can include a channel for cord 300 that separates cord 300 and lumen 312. Similarly, malleable section 138 can include loops or channels to guide or segregate cord 300.

Figure 11:
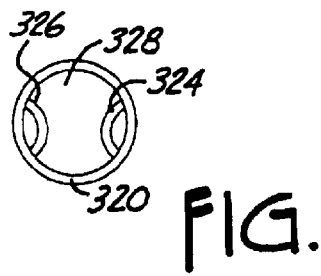
FIG. 11 is a sectional view of a shaft allowing for the passage of two control cords, the cross section being taken perpendicular to the axis of the shaft.

In the two cord embodiment of FIG. 2, cords 302, 304 extend through shaft 320 and malleable section 136. Shaft 320 can include separate guide loops 324, 326, as shown in the cross section in FIG. 11. Alternatively, shaft 320 can include channels for cords 302, 304 that separate cords 302, 304 from lumen 328, as an alternative to guide loops which just guide the cords. Similarly, malleable section 136 can include loops or channels to guide and/or segregate cords 302, 304.

Figure 13:
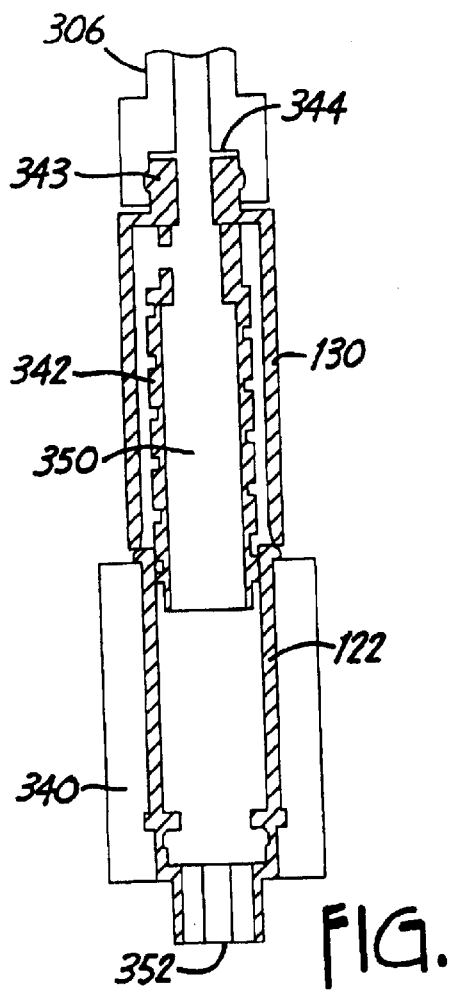
FIG. 13 is a sectional view of the handle and knob of FIG. 12 taken along line 13—13 of FIG. 12.
Figure 12:
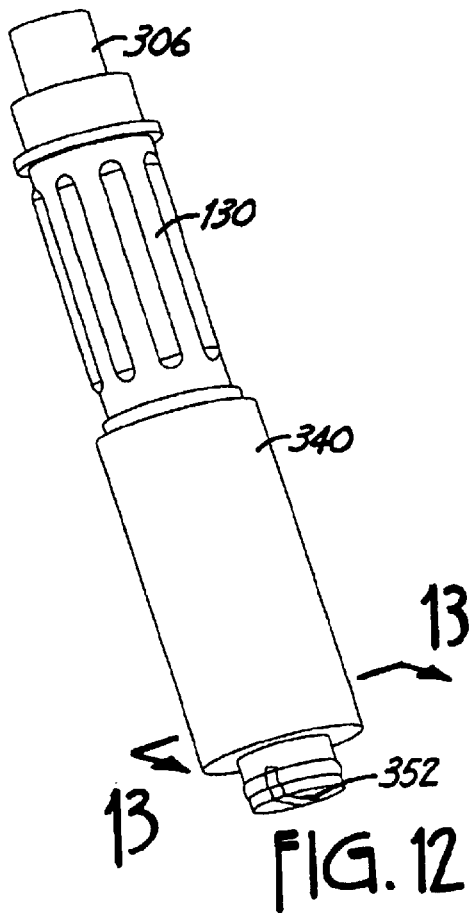
FIG. 12 is a perspective view of a handle and knob for use with a directional medical device with a single control cord.

The control mechanism includes a transfer component connected to the knob. This transfer component transfers the torque applied to the knob to induce forces on the strands or other communication conduits. An embodiment of a control mechanism suitable for a one cord based communication conduit is shown in FIG. 3. In FIG. 3, hidden structure of control mechanism 338 within handle 122 is shown for clarity. A perspective view of this embodiment is shown in FIG. 12, and a cross sectional view is shown in FIG. 13.

Knob 130 rotates relative to handle 122 and shaft 306. As shown in FIGS. 12 and 13, handle 122 includes a grip 340. Knob 130 connects with shaft 306 at interlocking segment 343. Interlocking segment 343 can include ball bearings, snap fits or the like to facilitate rotation of knob 130 and optional stops to interlock the adjacent components. Interlocking segment 343 fits within flanges 344 at the proximal end of shaft 306. Knob 130 similarly interlocks with handle 122 such that knob 130 can appropriately rotate.

Threaded shaft 342 is located within knob 130 and handle 122. As shown in FIG. 3, cord 300 is mechanically fastened, clipped, soldered or similarly connected to threaded shaft 342 at member 344. Knob 130 includes mated threads 346 such that rotation of knob 130 moves threaded shaft 342 within knob 130 and handle 122. Movement of threaded shaft 342 applies corresponding tension to cord 300. An open lumen 350 extends through shaft 306, knob 130, threaded shaft 342 and handle 122 to opening 352, as shown in FIG. 13.

A control mechanism 358 for a two cord embodiment is shown in FIGS. 2 and 14–16. Knob 128 rotates relative to shaft 320 and handle 120. As shown in the cross section of FIGS. 16A and 16B, knob 128 joins with shaft 320 and handle 120 at interlocking segments 360, 362, respectively. Interlocking segments 360, 362 can include ball bearings, a snap fit or the like to facilitate the relative motion. Interlocking segments 360, 362 can include stops or the like to interlock the adjacent elements together.

Figure 16B:
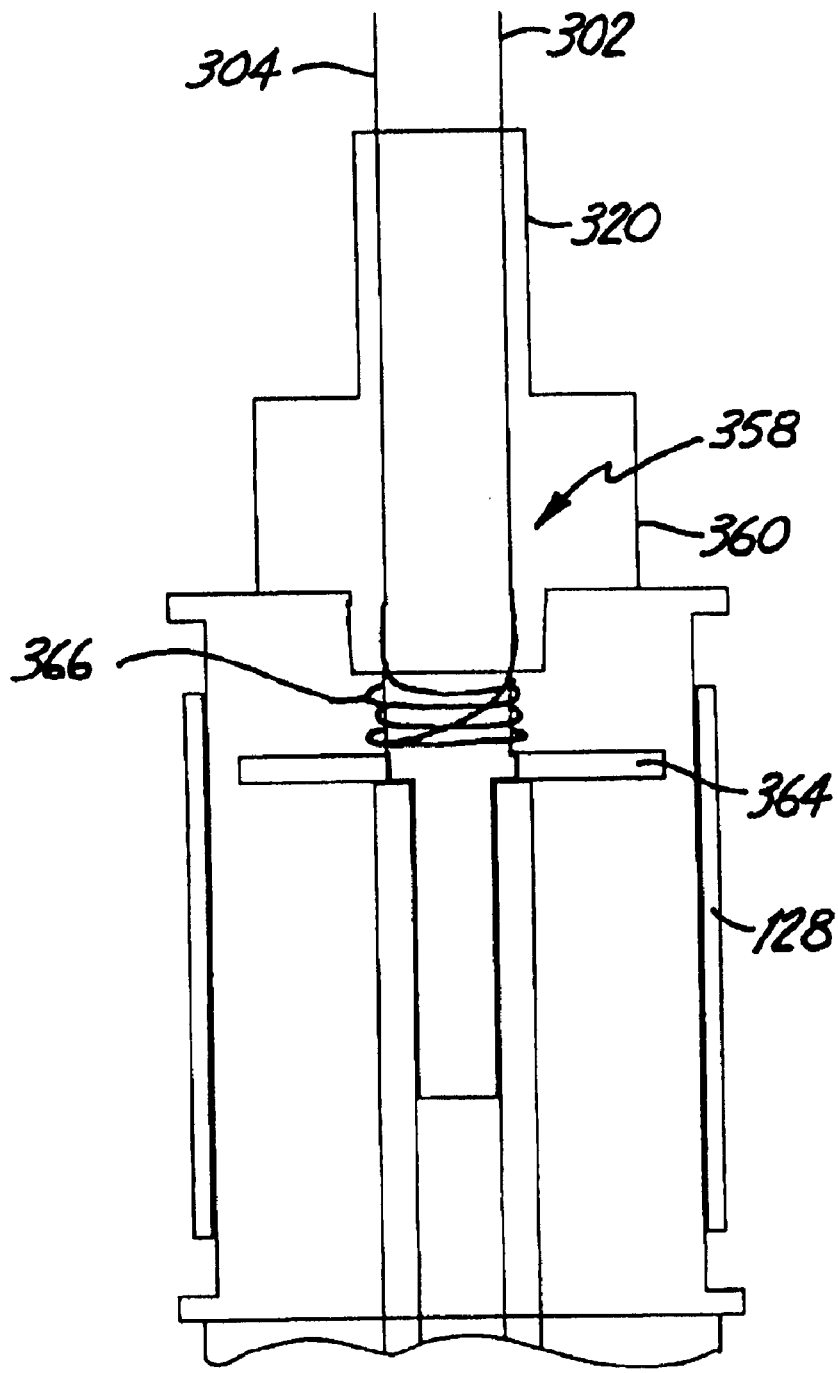
FIG. 16B is a sectional view of the handle and knob of FIG. 14 with the wing nut portion expanded and the cords shown.

Referring to FIGS. 2, 16A and 16B, a wing nut 364 is located within knob 128. Wing nut 364 is connected to knob 128 such that wing nut 364 rotates with knob 128. Wing nut 364 includes a notched portion 366 protruding toward shaft 320. Cords 302, 304 wrap around notched portion 366 of wing nut 364 such that one cord unwinds while the other cord winds onto the threads of wing nut 364 when knob 128 is rotated. A central lumen 370 extends from shaft 320 through wing nut 364, knob 128 and handle 120 to opening 372.

The use of two opposing cords, such as in the embodiments in FIGS. 2 and 14–16, provide a locking bendable tip 148. One cord provides tension that prevents extension of the bent tip while the second cord prevents further bending of the tip. Thus, the two cord embodiment is preferred for applications where a locked tip is desired for holding an instrument in a rigid orientation. Alternatively, to obtain locking of the articulating segments, notches 374 optionally can be placed on each of the hinge elements, as shown in FIG. 4. In these embodiments, the hinge ratchets between adjacent positions and locks in place when the cords are not applying force. Similarly, prongs on the flat portions of a segment 202 can engage notches in adjacent elements to lock the segments at a particular relative position until the cords are used to dislodge the prong and change the position.

In alternative embodiments, cords can be replaced with other analogous structure to apply asymmetric tension/extension along edges of the tip to cause bending of the tip. For example, cords can be replaced with a hydraulic system with thin tubes containing hydraulic fluid. Sealed pistons are located at each end of the tube to transfer movement at one end of the tube to opposite movement at the other end through the hydraulic fluid.

The directional medical devices described herein are used to deliver a medical instrument to a desired location within a patient. The instrument can be permanently attached to the end of the bendable tip. Alternatively, the instrument can be reversibly attached to the bendable tip. For example, instrument 400 can be attached to a securing section 402, as shown in FIG. 17. Securing section 402 reversibly attaches to the tip of the directional medical device. In the embodiment of FIG. 17, securing section 402 includes notches 404, 406 that engage prongs 232 of the tip embodiment shown in FIGS. 4, 7 and 8. Alternative attachment mechanisms, such as a screw mechanism or a bayonet mechanism, can be used to reversibly attach the medical instrument to the tip.

As shown in FIG. 17, control cable 408 extends from securing section 402. Control cable 408 can be threaded through the central lumen of the directional medical device to the proximal end of the device. Control cable 408 can be attached to an actuator or the like, an automated instrument or manually manipulated for control of instrument 400. The nature of cable 408 depends on the characteristics of instrument 400. For example, cable 408 can be a fiber optic element for visualization or transmission of laser light, a power cord connected to transducers or electrodes, or a mechanical cord to control movements of components of instrument 400.

In other alternative embodiments, the instrument is moved in and out of position at the end of the tip through the central lumen of the directional medical device 100. These embodiments provide constraints on the sizes of both the instruments and the lumen since clearly the instrument must have a diameter smaller than the minimum diameter of the lumen. However, these embodiments provide added flexibility for performing the medical procedure since more than one instrument can be used, and instruments can be used that require the movement of components of the instrument into and out of the patient for use of the instrument during the procedure.

As noted above, a central lumen or a plurality of lumens generally connects the tip with an opening at the proximal end of directional medical device 100. The lumen provides for passage of medical instruments and/or cables needed to operate a medical instrument at the tip. The size of the lumen extending through the length of the device can be selected to provide the desired degree of access between the tip and the proximal end of the device. For example, if instruments are mounted on the end of the tip, only a narrow lumen may be needed to provide for a cable or the like to extend from the tip to an actuator at the proximal end of the device. However, if the instrument or components of the instrument are moved through the lumen between the proximal end and the tip, the diameter of the lumen may need to be larger to accommodate the instrument or component of the instrument. Generally, the lumen has a width of from about 0.5 mm to about 8 mm, and alternatively from about 1 mm to about 6 mm.

Referring to FIG. 1, a suitable actuator 114 can be used to control the operation of medical instrument 112 positioned at bendable tip 108. The nature of the actuator depends significantly on the nature of the instrument. For example, a visualization instrument may have a fiber optic cable or the like for receiving the signal and a power cable for transmitting electricity to the instrument. The fiber optic can be connected to a suitable display, and the power cable can be connected to a suitable power source. The actuator can be a power switch which can be positioned on handle 102 or, alternatively, separate from the handle where the power cord and fiber optic exit from the central lumen of the device.

In general, the location of the actuator would be influenced by the connection between the instrument 112 and the directional medical device 100. If the instrument is permanently attached to tip 108, actuator 114 can be built into handle 102 with a permanent connection by way of a cable or the like to instrument 112. If instrument 112 is releasably mounted onto tip 108 prior to the start of the procedure, it may or may not be convenient to use an actuator 114 mounted on handle 102. A cable from instrument 112 can be attached to an actuator on handle 102 or the cable can exit the lumen and connect to an actuator separate from handle 102.

If the instruments are inserted and removed through a lumen during the procedure, a separate actuator is generally more convenient, perhaps connected to a separate handle used to control the movement of the instrument. For example, a gripper and fastener applicator connected to a single shaft can connect to a handle with one actuator, such as a lever or knob, for the gripper and a second actuator to control the fastener applicator. Some instruments require very specific controls, while other instruments require introduction and removal of components which can be performed conveniently manually. Based on the discussion herein, a reasonable configuration can be adopted to operate both the directional medical device with a bendable tip as well as corresponding medical instruments.

Suitable instruments for use with the directional medical device described herein include, for example, lenses or transducers for imaging, visualization or laser transmission, electrodes for tissue ablation, electrodes for cauterization, fasteners, cutting blades, forceps and combinations thereof. Preferred devices include, for example, grippers and fastener applicators. In particular, preferred grippers and fastener applicators are suitable for fastening leaflets of vascular valves or heart valves. Thus, the instruments can be used to correct valve insufficiencies. Preferred grippers and fastener applicators are described further below.

Fastener Applicators and Grippers

Preferred procedures using the directional medical devices described herein include, for example, medical procedures correcting natural valve insufficiencies by attaching valve leaflets together. To attach opposing leaflets of a natural vascular valve or heart valve, the leaflets are gripped and a fastener is deployed that pierces two or more leaflets. A single instrument can simultaneously grip the leaflets while deploying the fastener.

Alternatively, two or more separate instruments can be used with at least one instrument performing the gripping while a second instrument deploys the fastener. If two or more instruments are used, they generally require distinct control cables to separately control the plurality of instruments. If a plurality of instruments are used, they can be deployed with a single directional medical device or with multiple directional medical devices.

Regardless of the number of instruments associated with a single directional medical device, the instruments can be permanently mounted at the end of the bendable tip, reversibly mounted at the end of the tip or selectively inserted from the proximal end of the device through the lumen to extend from the tip. One or more cables generally span the lumen for each instrument to control the instrument and/or position the instrument. If the instrument is in place at the tip of the directional medical device prior to initiating the medical procedure, the corresponding cables can be appropriately connected at the proximal end of the device with an actuator or instrument.

If multiple instruments, such as a separate gripper and a fastener applicator, are deployed through the lumen of the directional medical device, the sizes of the lumen and the instruments must be appropriate to permit both instruments to be simultaneously deployed at the tip of the device. However, generally the instruments can be inserted or removed one at a time through the lumen of the device. The cable that remains extending through the lumen when the instrument is at the tip of the device may or may not be thinner than the corresponding instrument.

Referring to FIGS. 18–25, an embodiment of a fastener applicator is depicted that can simultaneously grip the leaflets and fasten them. However, the fastener applicator can optionally be used with a separate gripper. This fastener applicator uses a fastener clip 440 which includes a first portion 442 and a second portion 444. Referring to FIGS. 20 and 21, first portion 442 includes spikes 446 extending from a first surface 448 of base 450. Base 450 has notches 452 at the edge of second surface 454 at a position rotated 90 degrees relative to spikes 446. The center of base 450 has an opening 456 with wings 458 oriented toward notches 452. Second surface 454 includes indentations 460 adjacent opening 456 oriented toward spikes 446.

Referring to FIGS. 22–24, second portion 444 includes perforations 466 which have a diameter equal to or slightly smaller than spikes 446. Tabs 468 extend from first surface 470 of base 472. Tabs 468 include lips 474 that can engage notches 452. Base 472 includes an opening 478 with wings 480. Base 472 is slightly noncircular to allow for tabs 468.

FIG. 25 displays first portion 442 engaged with second portion 444. When portions 442, 444 are engaged, spikes 446 engage perforations 466 and tabs 468 engage notches 452. The leaflets are positioned in the separation between base 450 and base 472.

Referring to FIG. 18, to deploy clip 440, first portion 442 is positioned with first applicator 480. First applicator 480 includes a central core 482 with a knob 484 at the end of the central core 482, as shown in FIG. 18A. Knob 484 engages indentations 460 when first portion is positioned on first applicator 480, and can pass through wings 458 when oriented accordingly for removal of first applicator 480. First applicator 480 also includes tubular portion 488, which slides over central core 482. When knob 484 engages indentations 460 and tubular portion 488 engages first surface 448, first portion 442 is held firmly by first applicator 480.

Referring to FIG. 19, second applicator 490 is used to engage second portion 444 with first portion 442. Second applicator 490 can push second portion 444 into place, or, alternatively, second applicator 490 can hold second portion 444 using a fastener such as threads or a clamp, as first portion 442 is pulled against it. After second portion 444 engages first portion 442, second applicator 490 is removed through directional medical device 100. Central core 482 is removed by first rotating knob 484 such that knob 484 passes through wings 458 and 480. Clip 440 remains fastened to the valve leaflets.

Clip 440 can be positioned at the end of the bendable tip prior to insertion of the directional medical device into the patient. Alternatively, second portion 444 or both first portion 442 and second portion 444 can be inserted through the lumen of the directional medical device after the device is deployed within the patient at the desired locations. A larger lumen is needed to deploy clip 440 or a portion of clip 440 through the lumen. With first portion 442 of clip 440 positioned near the leaflets, a separate gripper can be used to grab the leaflets prior to securing the leaflets with spikes 446. The separate gripper can be deployed through the lumen of the directional medical device or using a second directional medical device.

Figure 26:
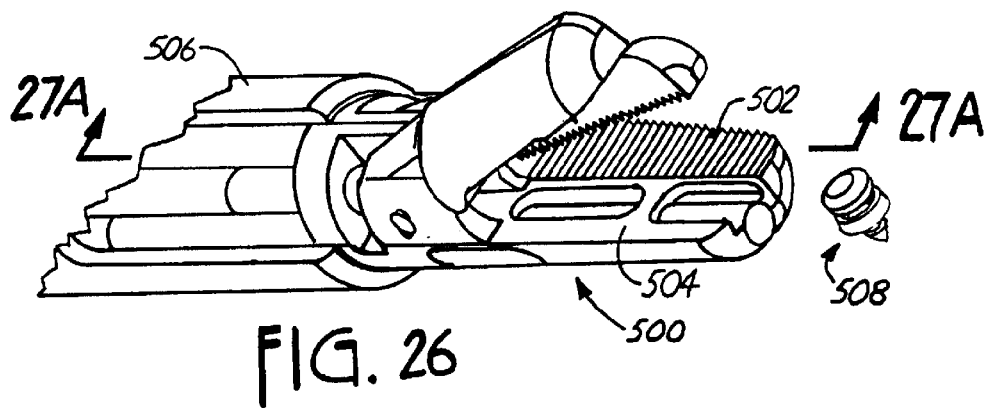
FIG. 26 is fragmentary, perspective view of a gripper mounted adjacent a fastener applicator on a single shaft.

In alternative embodiments, a distinct gripper and fastener applicator are used to secure the edges of the opposing leaflets together. Referring to FIG. 26, instrument 500 includes a gripper 502 and a fastener applicator 504 that extend from a shaft 506. The relative position of gripper 502 and fastener applicator 504 can be reversed. In this embodiment, gripper 502 can first grab the leaflets. Then, fastener applicator 504 can apply a fastener 508 on captured leaflet edges to secure the leaflets.

Figure 27A:
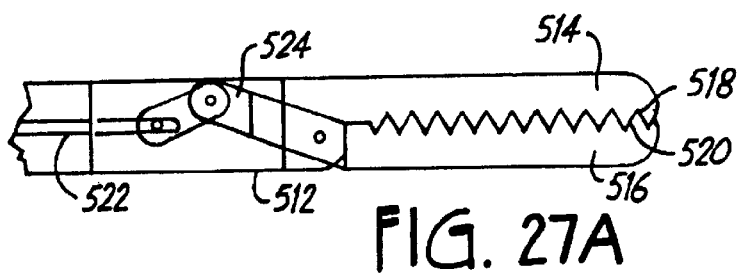
FIG. 27A is a sectional side view of the gripper of FIG. 26 taken along line 27A—27A of FIG. 26.

One embodiment of gripper 502 is depicted in more detail in FIG. 27A. In this embodiment, claw gripper 512 has opposing jaws 514, 516, which meet at serrated edges 518, 520 in a closed orientation. Serrated edges 518, 520 assist with the gripping of the valve leaflets. The extension of rod 522 alters the relative position of jaws 514, 516 by moving a lever 524. Rod 522 extends to the proximal end of the device such that a physician can manipulate rod 522 outside of the patient. The length of jaws 514, 516 should be appropriate for the jaws to reach the leaflets at the maximum anticipated spacing between the leaflets.

Figure 27B:
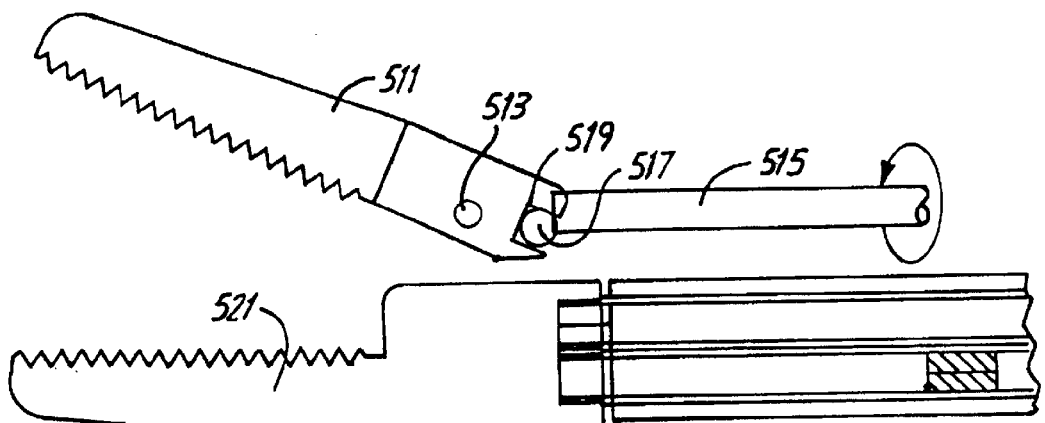
FIG. 27B is an exploded, sectional side view of an alternative embodiment of the gripper of FIG. 27A, the alternative embodiment being based on a cam, where the rod and moveable jaw have been removed from the remainder of the gripper.
Figure 27C:
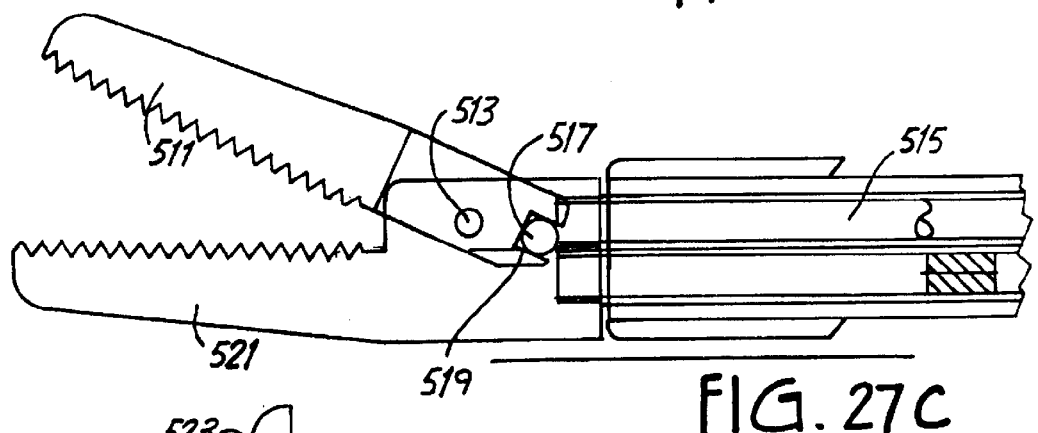
FIG. 27C is a sectional side view of the embodiment shown in FIG. 27B.
Figure 27D:
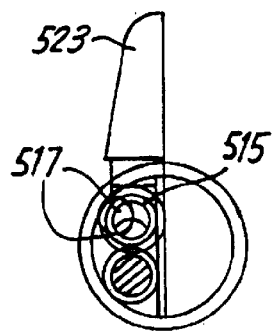
FIG. 27D is a view down the end of the shaft from the proximal end toward the jaws, where the ball of the cam is shown in both an open and closed position.

As an alternative to the lever mechanism shown in FIG. 27A, a cam can be used to rotate the jaw, as depicted in FIGS. 27B–D. In particular, jaw 511 rotates around pivot 513. Rotation of rod 515 causes ball 517 to change position relative to the position of rod 515. Ball 517 fits into track 519 in the end of jaw 511. Also, ball 517 fits into a notch in an off center position in the end of rod 515 such that rotation of rod 515 moves ball 517 up or down. Lowering of the ball results in the opening of jaw 511 relative to jaw 521. Rod 515 is rotated using lever 523, as shown in FIG. 27D. Generally a 180 degree rotation of rod 515 results in motion of jaw 511 from a closed position to its open position.

Figures 28A, 28B, 28C, 28D:
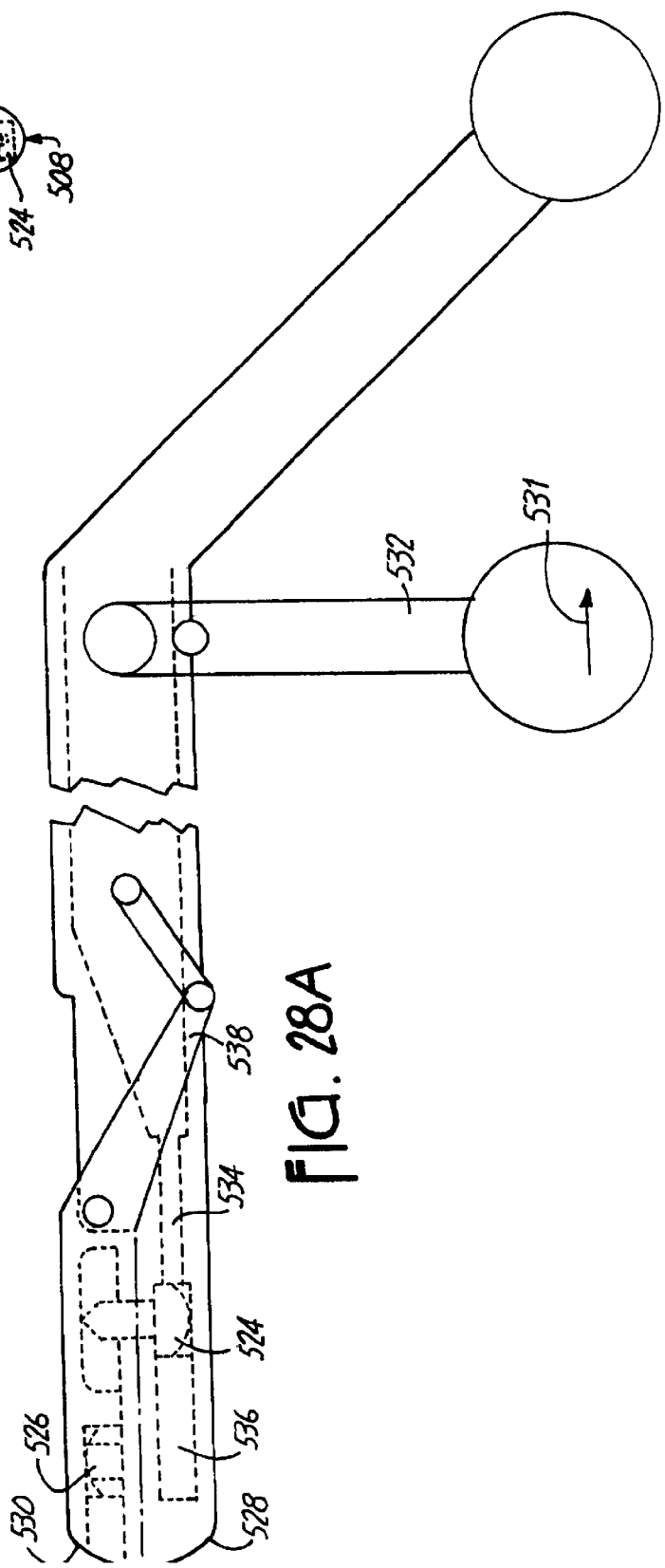
FIGS. 28A–C are side views of the fastener applicator of FIG. 26 where the view in FIG. 28B is taken at a right angle relative to the views in FIGS. 28A and 28C. Hidden structures are shown with phantom lines.
FIG. 28D is a side view of the tack and cap of FIG. 28A secured together, shown in phantom.

As depicted in FIG. 26, fastener applicator 504 applies a fastener 508. Further details about fastener applicator 504 can be seen in FIGS. 28A–C. Fastener applicator 504 holds tack 524 and cap 526 in separate housings for deployment. When jaws 528, 530 are opened by the movement of lever 532 in the direction shown by the arrow 531 in FIG. 28A, rod 534 slides tack 524 within track 536 to a position aligning cap 526 with tack 524, as shown in FIGS. 28B and 28C. Jaws 528, 530 rotate relative to each other by way of lever arm 538 or other mechanical link, such as a cam. When jaws 528, 530 subsequently are closed, tack 524 engages cap 526, as shown in FIG. 28D, thereby fastening the leaflets. Jaws 528, 530 can be opened to release tack 524 and fastened leaflets.

If desired, gripper 502 and fastener applicator 504 can be positioned at the end of the directional medical device prior to insertion of the medical device into the patient. Alternatively, gripper 502 and/or fastener applicator 504 can be deployed through the lumen of the device. Generally, for this embodiment, the minimum diameter of the lumen must be larger to provide for passage of gripper 502 and fastener applicator 504. In either case, gripper 502 and fastener applicator 504 can be fixed relative to each other or moveable relative to each other at least a small distance to facilitate the separate functions.

Figure 29:
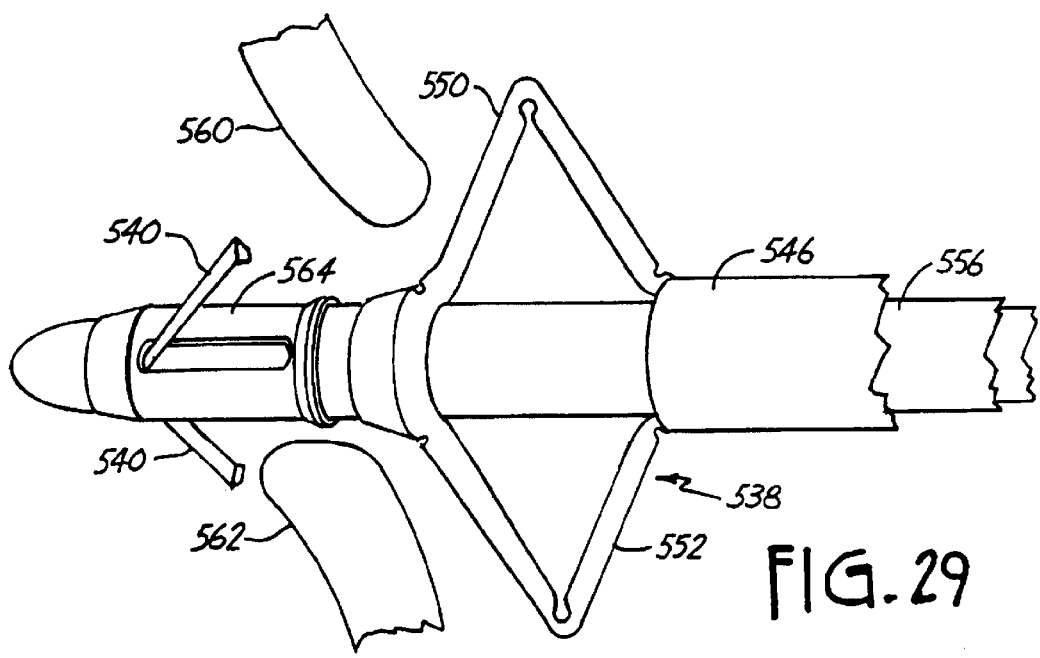
FIG. 29 is a side view of a gripper with a plunger used to direct the leaflets to gripper arms.

In alternative embodiments, the gripping functions and the fastening functions are performed with completely distinct instruments. Referring to FIG. 29, gripper 538 includes graspers 540 used to grasp each leaflet. To push the leaflets toward graspers 540, plunger 546 includes two or more arms 550, 552.

Shaft 556 can be pulled to draw spring loaded graspers 540 toward plunger 546 to grip leaflets 560, 562 within grasper 540. Alternatively, plunger 546 can push leaflets 560, 562 toward graspers 540. In any case, as plunger 546 reaches a certain position relative to graspers 540 so that graspers 540 are within reach of leaflets 560, 562, shaft 556 is pulled back to retract graspers 540, which clasp leaflets 560, 562 between graspers 540 and grasper tube 564. Once leaflets 560, 562 are clasped, plunger 546 can be removed. After leaflets 560, 562 are fastened, graspers 540 can be released by extending shaft 556 such that gripper 538 can be withdrawn. Graspers 540 should be less than about 10 mm in length. Graspers 540 can be curved.

Gripper 538 can be placed at the tip of the directional medical device prior to deployment of the medical device within the patient or gripper 538 can be deployed from the proximal end of the device after the device is placed within the patient. Arms 550, 552 can be made of spring like material such that the arms extend after they are free from the lumen and fold to a flattened position when pulled against the opening to the lumen at the tip of the device.

Figure 30:
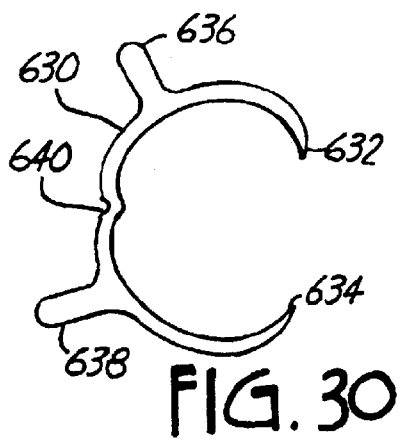
FIG. 30 is a side view of a crimp ring in an uncrimped position.
Figure 31:
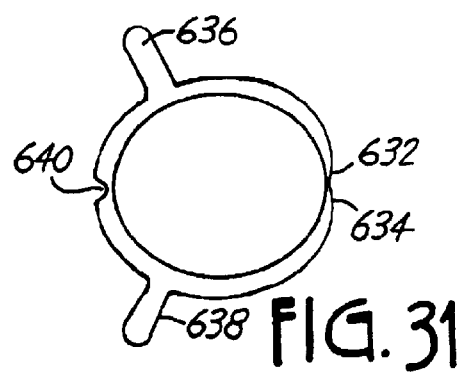
FIG. 31 is a side view of the crimp ring of FIG. 30 following crimping.

Once the leaflets are gripped any of a variety of fasteners can be used to fasten two or more leaflets together. One suitable fastener is shown in FIGS. 30 and 31. Referring to FIGS. 30 and 31, crimp ring 630 includes points 632, 634 and handles 636, 638. Between handles 636, 638 is a notch 640. Notch 640 provides a weak location for bending points 632, 634 toward each other, as shown in FIG. 31. Crimp ring 630 is placed near the grasped leaflets. Then, handles 636, 638 are rotated away from each other to place the crimp ring 630 in the closed crimped position shown in FIG. 31 with points 632, 634 piercing respective leaflets.

Figure 32:
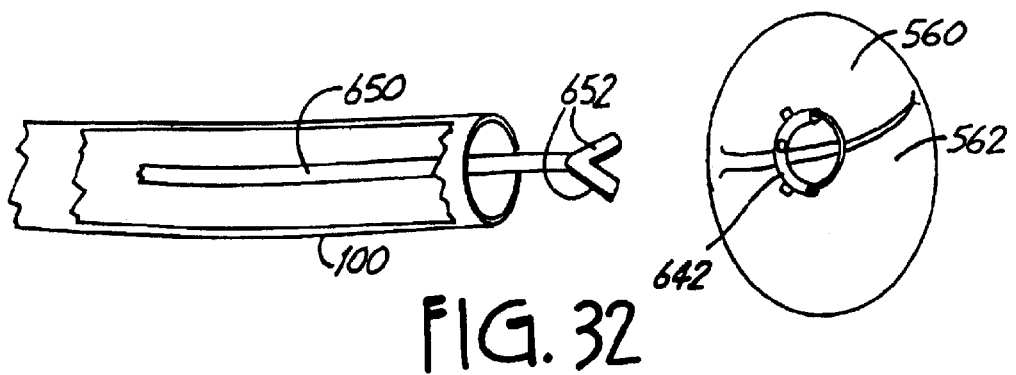
FIG. 32 is a perspective view of a ring fastener being positioned with an applicator toward heart valve leaflets, where a portion of the cardiac catheter is cut away to permit the visibility of structure within the catheter.
Figure 33:
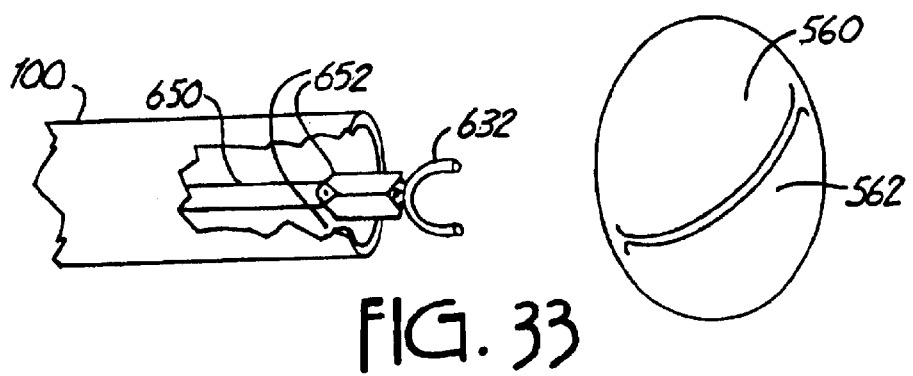
FIG. 33 is a perspective view of the applicator of FIG. 32 following deployment of the ring fastener.

Rings such as crimp ring 630 can be applied with an applicator 650, as depicted in FIGS. 32 and 33. Ring 630 is brought up to leaflets 560, 562 and deformed to pierce leaflets 560, 562. Applicator 650 can include lever arms 652 and/or other implements to assist with deployment of ring 630. Lever arms 652 hold handles 636, 638 and rotate handles to crimp the ring to bring points 632, 634 toward each other.

As with gripper 538, crimp ring 630 can be positioned at the end of directional medical device 100 prior to placement into the patient, or crimp ring 630 can be deployed from the distal end when device 100 is already within the patient.

Further description of gripping and fastening instruments for performing mitral and tricuspid valve repairs is found in copending and commonly assigned U.S. patent application Ser. No. 09/115,820, now U.S. Pat. No. 6,165,183 to Kuehn et al., entitled "Mitral and Tricuspid Valve Repair," incorporated herein by reference.

Surgical Procedures

As noted above, various procedures can be performed using the directional medical device described herein. The directional medical devices can be introduced through an opening in the body of the patient. Suitable openings include natural body openings as well as surgical openings. For example, the directional medical device can be used in surgical open procedures, such as an open chest procedure. These devices can also be used in the performance of less invasive medical procedures, commonly called minimally invasive medical procedures. These less invasive medical procedures generally involve a small incision that allows for the introduction of instruments into the body. These less invasive procedures include, for example, thoracotomies, entries into a vein or artery and small incisions in the chest providing access to the heart.

As described in detail herein, suitable procedures for the use of the directional medical device with a bendable tip include procedures to repair heart valves. In preferred embodiments of the heart valve repair procedures, the repairs are performed on a beating heart. Alternatively, the heart can be stopped during the procedure. Cardioplegia, i.e., stopped cardiac contraction, can be induced by certain chemicals such as cold potassium containing solutions that are introduced into the myocardium. The chemical induction of cardioplegia requires the isolation of the heart and ascending aorta from the rest of the patient's vascular system. Procedures using cardioplegia are less desirable since they require cardiopulmonary bypass, which increases patient risk factors.

In particular, less invasive heart valve repair procedures can be performed on a beating heart. These less invasive procedures can be performed by a vascular approach or by entry into the heart through a small incision in the chest. For entrance through the chest wall, a pathway into the heart can be established using a type of catheter that can be termed a cardiac catheter. The cardiac catheter generally has suitable dimensions for deployment and insertion into a human heart in the vicinity of the mitral or tricuspid valve. The cardiac catheter generally has an elongated tubular section and proximal and distal ends each with an opening. For example, the cardiac catheter can be a catheter introducer used for standard intravascular placement or a similar instrument. The proximal end of the cardiac catheter preferably includes a hemostasis valve to prevent blood from flowing out of the cardiac catheter.

The tubular section of the cardiac catheter preferably is flexible so that it can be guided through the body to the desired location. Generally, the tubular section has a length from about 4 cm to about 15 cm and a diameter from about 3 mm (9 French (F)) to about 10 mm (30 F), more preferably from about 3 mm (9 F) to about 8 mm (24 F). However, the tubular section can be selected to have a suitable length appropriate for the specific procedure used. The tubular section preferably has a tapered end to assist with introduction of cardiac catheter into the heart.

For cardiac catheter based procedures, one or more access points are used along the patient's chest, generally positioned between adjacent ribs. The access points provide access to the heart. Incisions are made to initiate the access points. Trocar sheaths, such as those used for the performance of laparoscopic procedures, can facilitate use of the access points as described in published PCT application WO 94/18881 to Stanford Surgical Technologies, Inc., incorporated herein by reference. Alternatively, soft tissue retractors, such as those used in pediatric open chest procedures, can be utilized to facilitate use of the access points. Suitable location of the access point(s) can be determined based on the approach appropriate for the gripper/fastener applicator to be used.

Once the heart is accessed, a guide wire can be inserted through the wall of the heart either near the apex of the heart into the left ventricle or near the top of the heart into the left atrium to access the mitral valve. Similarly, the right side of the heart can be accessed to perform tricuspid valve repairs. A dilator can be slid over the guide wire to expand the opening into the heart. Suitable guide wires and dilators are available from Daig Corp., Minnetonka, Minn. A cardiac catheter with a hemostasis valve is deployed over the dilator. The cardiac catheter provides access into the heart to deliver the repair device or devices. In particular, the directional medical devices described herein can be introduced through the cardiac catheter to position the bendable tip near a heart valve to be repaired.

Alternatively, a cardiac catheter can be inserted through an incision in the wall of the heart at the desired location. As during normal cannulation, a purse string suture can be applied at the point where the cardiac catheter enters the heart to reduce any bleeding. The suture can be applied, for example, using a piece of suture with a needle on both ends. The needles can be manipulated using forceps or the like. After the desired stitching is performed, the needles can be cut off using endoscopic scissors. Additional cardiac catheters can be placed near or into the heart, as desired.

Once the cardiac catheter is in place, the directional medical device with associated gripper/fastener instruments can be directed at the mitral or tricuspid valve to perform the repair. All of the instruments are designed such that the appropriate manipulations by the appropriate health care professional are performed at the proximal end of the cardiac catheter.

Following completion of the edge-to-edge repair, the cardiac catheter is removed. The procedures used to deploy the cardiac catheter preferably minimize the damage to the heart muscle by separating the tissue without significantly tearing the tissue. Nevertheless, stitches or staples can be used to close the incision at the point where the cardiac catheter was inserted. Once access to the heart has been closed, the incision providing access into the chest cavity is closed.

Alternatively, a less invasive, percutaneous vascular approach can be used. There are two, alternative, percutaneous vascular approaches to positioning the catheter for the medical procedure to repair the heart valves. One is to introduce the catheter into the femoral artery by a standard introducer sheath and advance it up the aorta, across the aortic valve into the left ventricle and then position its tip under the mitral annulus. This is commonly referred to as the "retrograde," approach.

The other approach, commonly referred to as the transseptal approach, is to introduce a transseptal. sheath apparatus, a long single plane curve introducer, into the right femoral vein and advance it through the inferior vena cava into the right atrium. From the right atrium, repairs can be performed on the tricuspid valve. To repair the mitral valve, a puncture is then made through the fossa ovalis in the intraatrial septum, and the apparatus is advanced into the left atrium where the trocar and dilator of the apparatus is removed, leaving the sheath in position in the left atrium. Once the valve is accessed, the repair can be completed as described above.

Edge-to-edge mitral valve repair provides a simple and effective repair technique relative to complex and surgically demanding approaches of chordal shortening, resectioning, chordal transposition or artificial chordae replacement. The edge-to-edge repair is particularly effective with severe isolated mitral regurgitation or in association with coronary artery bypass surgery. The directional medical device is a versatile instrument for the performance of these repairs. In some embodiments, the directional medical device can be used to deliver one or more instruments without removing the directional medical device. The bendable nature of the tip and optionally the malleable section, provide for better positioning for the use of a fastener during the procedure.

In some embodiments, the present approach provides the benefits of the edge-to-edge repair without the trauma of open heart surgery and cardiopulmonary bypass. Thus, the procedure can be accomplished concomitant with coronary artery bypass graft (CABG) or as a stand alone outpatient procedure in a cardiac catheterization laboratory. The advantages include reduced cost, hospitalization and patient recovery times. With minimal trauma to the patient, it may be desirable to perform the repair earlier before the disease has progressed to a serious level. Thus, more repair procedures may be performed, preventing further progression of the disease, obviating the need for more serious invasive procedures.

Similarly, relatively straightforward repairs of vascular valves can be performed using a small incision to access a patient's vein. Similar grippers and fasteners can be used to perform edge-to-edge fastening of the leaflets of the vascular valves. Thus, simplified forms of the heart valve repair procedures can be used to restore competence to vascular valves.

The instruments described above may be distributed in the form of a kit. For example, the kit can include a directional medical device with a bendable tip and a suitable cardiac catheter or other catheter for a vascular approach to perform minimally invasive surgical procedures. The kit can include a medical instrument attached to the bendable tip, one or more medical instruments for releasable attachment to the tip or one or more medical instruments that can be introduced through the lumen of the directional medical device. The components of the kit can be packaged together as a sterile assembly in a tray with a sealed pouch or the like covering the tray. If some parts are disposable, such as the shaft, malleable section and tip, while other parts are reusable, such as the handle and instruments, the disposable parts can be sold separately from the reusable parts.

For the performance of heart valve repair, the kit generally includes a fastener applicator. The kit may also include a suitable gripper for use with the fastener applicator. The kit preferably includes instructions for the performance of mitral and/or tricuspid valve repair. In particular, the instructions can describe the particular use of the fastener applicator and/or the grippers.

The embodiments described above are intended to be illustrative and not limiting. Additional embodiments are within the claim. Although the present invention has been described with reference to preferred embodiments, workers skilled in the art will recognize that changes may be made in form and detail without departing from the spirit and scope of the invention.

What is claimed is:

1. A device for medical procedures comprising:
   a shaft having a rigid section at a proximal end;
   a bendable tip comprising a plurality of articulated segments arranged at a distal end of the shaft; and
   an end segment extending from the bendable tip, wherein the end segment comprises a plurality of instrument deploying elements.

2. The device of claim 1 wherein the bendable tip has suitable dimensions for insertion into a human heart.

3. The device of claim 1 wherein the bendable tip can bend in either of two opposite directions in a plane relative to a linear configuration.

4. The device of claim 1 wherein the bendable tip further comprises a plurality of independent pivoting segments pivotable with respect to adjacent segments.

5. The device of claim 4 wherein each pivoting segment of the bendable tip is connected to an adjacent segment at two coaxial hinges.

6. The device of claim 1 wherein the bendable tip can be locked at a selected degree of bend.

7. The device of claim 1 further comprising two communicating elements extending from the bendable tip to the proximal end of the shaft, the communicating elements connecting to the bendable tip such that each communicating element functions as an opposing lever arm with respect to the bending of the tip.

8. The device of claim 1 further comprising a single communicating element extending from the bendable tip to the proximate end of the shaft, the communicating element being connected to the bendable tip such that tension on the communicating element tends to bend the bendable tip in one direction relative to a linear configuration.

9. The device of claim 1 further comprising a malleable section between the rigid section and the bendable tip.

10. The device of claim 1 further comprising:
    a handle having an elongated grip generally coaxial with the shaft and being attached to the rigid section of the shaft;
    the grip comprising a knob rotatable about the longitudinal axis of the handle; and a first cord connecting the bendable tip with the knob such that rotation of the knob changes the position and degree of bending of the tip.

11. The device of claim 10 further comprising a second cord connecting the bendable tip with the knob wherein rotation of the knob in one direction extends the first cord while retracting the second cord and rotation of the knob in the other direction extends the second cord while retracting the first cord.

12. The device of claim 1 wherein the plurality of instrument deploying elements at least include a first instrument deploying element and a second instrument deploying element, wherein the first instrument deploying element comprises a lumen centrally located in the end segment, the lumen being adapted for introducing an instrument through the end of the bendable tip, and the second instrument deploying element comprises at least two tabs extending from the end segment, the tabs being adapted to releasably secure another instrument therebetween.

13. The device of claim 12 further comprising a gripper extendible through the lumen from the end segment of the bendable tip.

14. The device of claim 1 wherein the articulated segments comprise at least one off-center channel having a cord extending through the channel to the proximal end of the shaft.

15. The device of claim 1 wherein the bendable tip has an asymmetric opening extending therethrough.

16. The device of claim 1 wherein the articulating elements have a central lumen with an elongated cross section with the major axis of the lumen being perpendicular to a pivot axis.

17. The device of claim 1 wherein adjacent articulating segments have hinge elements that snap into position.

18. The device of claim 1 wherein the plurality of instrument deploying elements at least includes a first instrument deploying element wherein the first instrument deploying element comprises a lumen centrally located in the end segment, the lumen being adapted for introducing an instrument through the end of the bendable tip.

19. The device of claim 1 wherein the plurality of instrument deploying elements at least includes a second instrument deploying element, wherein the second instrument deploying element comprises at least two tabs extending from the end segment, the tabs being adapted to releasably secure another instrument therebetween.

20. A device for medical procedures comprising:
a shaft having a rigid section;
a malleable section extending from the rigid section of the shaft;
a bendable tip comprising a plurality of articulated segments extending from the malleable section; and
a control mechanism arranged at a proximal end of the shaft and being connected to the bendable tip by at least one cord, the control mechanism comprising a knob rotatable about the longitudinal axis of the shaft, wherein adjustment of the knob controls the position and degree of bending of the bendable tip by manipulation of the cord.

21. The device of claim 18 wherein the malleable section comprises a spring metal.

22. The device of claim 18 wherein the malleable section comprises a soft metal.

23. The device of claim 18 wherein the malleable section comprises a flexible polymer.

24. The device of claim 18 wherein a straight section connects the malleable section and the tip.

25. The device of claim 18 wherein the bendable tip comprises an end segment comprising a plurality of instrument deploying elements.

26. A device for medical procedures comprising:
a shaft with a distal end and a proximal end;
a bendable tip extending from the distal end of the shaft, wherein the bendable tip can bend in either of two opposite directions in a plane relative to a linear direction;
a handle having a grip generally coaxial with the shaft wherein the handle is attached to the proximal end of the shaft;
the grip comprising a knob rotating around the axis of the grip;
a first cord connecting the tip with the knob such that rotation of the knob in one direction retracts the cord to bend the tip; and
an end segment extending from the bendable tip, wherein the end segment comprises a plurality of medical instrument deploying elements extending from the end segment.

27. The device of claim 24 further comprising a second cord connecting the tip with the knob wherein rotation of the knob in one direction extends the first cord while retracting the second cord and rotation of the knob in the opposite direction extends the second cord while retracting the first cord.

28. The device of claim 24 wherein the cord is connected to the tip such that tension on the cord tends to bend the tip in one direction relative to its linear configuration.

29. The device of claim 24 wherein the end segment further comprises at least two tabs extending from the end segment, the tabs being adapted to releasably secure a medical instrument comprising a fastener applicator.

30. The device of claim 24 wherein the end segment further comprises a lumen centrally located in the end segment, the lumen being adapted for introducing a medical instrument comprising a gripper through the end of the bendable tip.

31. The device of claim 24 wherein the end segment further comprises a medical instrument deploying element for deploying an endoscope.

32. The device of claim 24 wherein the end segment further comprises a medical instrument deploying element for deploying an ablation element.

33. The device of claim 24 wherein the end segment further comprises a medical instrument deploying element for deploying an ultrasound probe.

34. The device of claim 24 wherein the end segment further comprises a medical instrument deploying element for deploying a transducer.

35. The device of claim 24 wherein the tip comprises a plurality of articulating segments.

36. The device of claim 24 wherein a lumen extends from the handle through the shaft to the tip.

37. The device of claim 34 further comprising a medical instrument extending from the tip, the medical instrument having a control element extending from the medical instrument to the handle through the lumen.

38. A method of repairing a heart valve comprising:
inserting a device into the heart, the device including a shaft, a bendable tip extending from the distal end of the shaft, an end segment extending from the bendable tip, the end segment being adapted to position and deploy a combination of different medical instruments, at least one medical instrument extending from the bendable tip; and
performing a repair of the heart valve with the medical instrument.

39. The method of claim 37 further comprising extending a catheter within the heart and wherein inserting the device into the heart comprises introducing the device through the catheter.

40. The method of claim 38 wherein the catheter extends into the heart through the wall of the heart.

41. The method of claim 38 wherein the catheter extends into the heart from the precava.

42. The method of claim 38 wherein the catheter extends through the septum separating the right atrium and the left atrium.

43. The method of claim 37 further comprising locking the bendable tip at a desired degree of bending.

44. The method of claim 37 wherein the bendable tip can bend in a plane in either of two opposite directions in a plane relative to a linear configuration.

45. The method of claim 37 wherein the bendable tip comprises a plurality of articulating segments.

46. The method of claim 44 wherein the device further comprises a malleable section between the shaft and the articulating segments.

47. The method of claim 37 wherein the device further comprises:
   a handle having a grip generally coaxial with the shaft wherein the handle is attached to the proximal end of the shaft;
   a knob rotating around the axis of the grip; and
   a cord connecting the bendable tip with the knob such that rotation of the knob changes the position of the cord to control the degree of bending of the bendable tip.

48. The method of claim 37 wherein the repair comprises fastening together the leaflets of a heart valve.

49. The method of claim 46 wherein the instrument comprises a fastener applicator.

* * * * *